(12) United States Patent
Wong

(10) Patent No.: US 8,167,853 B2
(45) Date of Patent: May 1, 2012

(54) SELF SERVICE CLEANING DEVICE FOR WOMAN

(75) Inventor: Chi Lan Wong, Macau (CN)

(73) Assignee: Ip Heong Wa, Andar, Macau ( * ) Notice: Subject to any disclaimer, the term of this patent is extended or adjusted under 35 U.S.C. 154(b) by 11 days.

(21) Appl. No.: 12/703,458

(22) Filed: Feb. 10, 2010

(65) Prior Publication Data
US 2010/0211021 A1   Aug. 19, 2010

(30) Foreign Application Priority Data

Feb. 16, 2009 (CN) .......................... 2009 1 0037201

(51) Int. Cl.
*A61M 31/00* (2006.01)
(52) U.S. Cl. ....................... 604/279; 604/275
(58) Field of Classification Search .................. 604/247, 604/279, 275
See application file for complete search history.

(56) References Cited

U.S. PATENT DOCUMENTS

| 6,537,260 | B1* | 3/2003 | Lamb ........................... 604/279 |
| 2005/0107752 | A1* | 5/2005 | Su et al. ........................ 604/275 |

\* cited by examiner

*Primary Examiner* — Jackie Ho
*Assistant Examiner* — Imani Hayman
(74) *Attorney, Agent, or Firm* — McNeely, Hare & War LLP; Kevin J. McNeely

(57) ABSTRACT

The present invention relates to a self service cleaning device for woman comprising a handle and a flexible conduit. The handle has a connector at its one end and is removably connected with a water supply pipe by the connector. The flexible conduit has one end connected with the handle and the other end which has a curved portion with a closed top corresponding to a curvature of vagina, wherein an opening is arranged at an introverted segment of the curved portion, and a plurality of outlets are orderly arranged on a circumferential surface of the curved portion, a plurality of circular protrusions are projecting outwardly and radially from the circumferential surface; and a counterflow preventer is arranged around an inlet of the flexible conduit. The present invention is low in cost, portable, simple in use, and good in cleaning effect, whereby it is easy to promote and widely adapted for effective prevention and treatment of diseases.

17 Claims, 5 Drawing Sheets

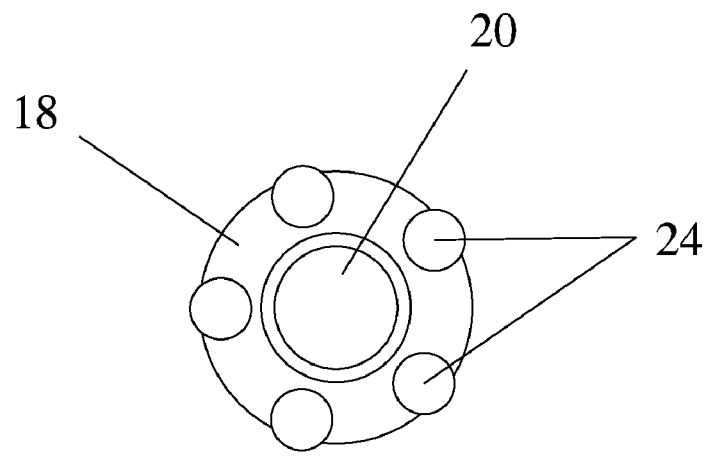
Fig. 4
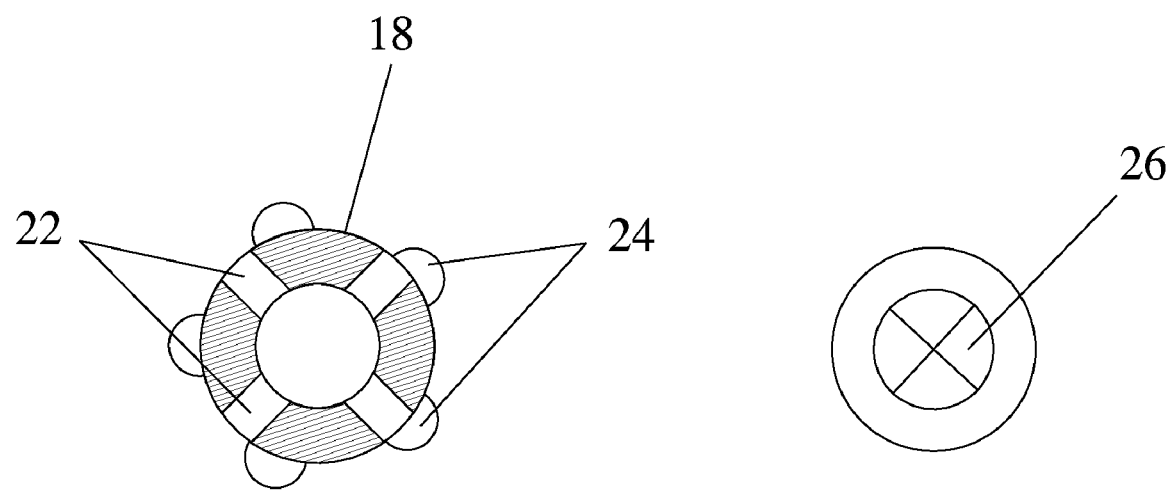
I - I
Fig. 5
Fig. 6

SELF SERVICE CLEANING DEVICE FOR WOMAN

CROSS REFERENCE TO RELATED APPLICATIONS

This utility patent application claims priority to Chinese patent application No. 200910037201.8 filed on Feb. 16, 2009.

TECHNICAL FIELD

The present invention relates to an apparatus for personal hygiene, and more particularly to a self service cleaning device for woman.

BACKGROUND OF THE INVENTION

Sexually transmitted diseases (STDs) are diseases transmitted by means of sexual contact or similar behaviors to cause infections of urinary reproductive organs and accessory lymphatic system. The STDs further include infections of non-reproductive organs, such as infections transmitted by direct contact from skin to skin, skin to mucosa, and mucosa to mucosa. The STDs may be involved with lesions of major systematic organs to cause severe infections of mouth, pharyngeal, anus, rectum, and the like, and therefore are communicable diseases which may do severe damage to physical and mental health of people.

According to the estimations of WHO (World Health Organization), 50 million new cases of syphilis and 250 million new cases of gonorrhea occur throughout the world every year. In addition, AIDS has been spread widely to over 210 countries of five continents since it was first recognized in homosexual men in USA in 1981. Up to the year 2002, around 70 million people worldwide were infected with HIV, and 20 million are dead.

In 1991, China announced the Regulations of "Prevention and control measures for sexually transmitted diseases", which prescribes that 8 types of venereal diseases including syphilis, gonorrhea, nongonococcal urethritis, condyloma acuminata, genital herpes, chancroid, lymphogranuloma venereum and AIDS, are under severe monitoring of the state.

In 2001, it was reported that there are 795,612 cases of the above 8 venereal diseases in China. Most of the infections occur in people aged between 20 and 39, and an increasing number of women were being infected in recent years. In the end of 2002, the accumulated cases of HIV occurred throughout the state is 40,560 since a AIDS sufferer was first recognized in China on 1985. The cases of infections with AIDS is 2,639 and the number of death cases is 1,047.

It is understood that people are vulnerable to STDs, despite of their ages and gender, and there is no congenital immunity or acquired immunity to STDs.

Further, it is common for women to be infected with cervicitis. According to a general investigation, the incidence rate of women aged at 16-76 is about 45.3%, and the infection with cervical carcinoma tends to be more common in younger women. In China, 500 thousand new cases are found every year, and the highest incidence rate occurs in women aged at 36. The incidence rate is increased by 15-20% in comparison with the figures in 70s-90s.

In addition, more and more women are working as a career woman in recent years. Many of them ignore health problems due to the heavy workload and the shrinkage of personal space. They would only seek for help from physicians when symptoms are present, or they may buy douching device from pharmacies to do cleaning by themselves.

In view of the foregoing situations, the use of condom is widely suggested for the prevention of STDs, while the use of self service cleaning device for woman is also helpful. To this end, many cleaning devices for woman, such as douching devices, are made available in the market. However, the available douching devices are small in capacity and could not reach to fornix around the cervix because of the limitations of their configurations, such that the prevention and treatment effects of these devices are limited.

In addition, PRC Utility Model ZL200620056052.1 discloses a portable vagina douching device, which comprises a plastic connector 1, a rubber connecting pipe 2 and a vagina douching head 3. In use, the douching head 3 is threaded onto one end of the connecting pipe 2 and the connector arranged at the other end of the connecting pipe 2 is connected to a water tap. The douching head is inserted at a specific depth into the vagina, and then the water tap is turned on for douching. After screwing out the connecting pipe 2 from the douching head 3, the medication may be injected via the opening of the douching head 3 for medical treatment when needed. Obviously, the douching device provides relatively poor douching effect, and it is also inconvenient to operate.

U.S. Patent Application 2002/0055723 A1 discloses a vagina cleaning system for preventing pregnancy and sexually transmitted diseases, which comprises a vagina opener, a vagina cleaning-solution sprayer, a multiple-functional vagina cleaning solution, and a health-promoting bacteria introducer. In terms of the configuration of the system, the cleaning solution is delivered by spraying, which provides a relatively poor douching effect, and particularly, it is hard to cleanse the vaginal rugae and the fornix around the cervix. Further, the system comprises so many parts whereby it is inconvenient to operate.

US Patent Application U.S. 2003/0055399 A1 discloses a system for personal hygiene, which comprises a connector attachable to an output interface of a shower head for directing a fluid flow from the shower head through the connector; a flexible fluid conduit having a proximal end coupled to the connector to receive a fluid flow from the shower head and a distal end; and an applicator attached to the distal end of the fluid conduit for directing the fluid flow to a targeted area. Such a personal hygiene system provides an unsatisfactory douching effect and is hard to deliver a cleaning solution.

U.S. Pat. No. 7,211,061 discloses a vaginal cleansing swab comprising an applicator shaft with first and second ends; a moisture absorbent end piece positioned over said first end of said applicator shaft and having a dome-shaped tip and more than one projecting disc-like portions, the diameters of said projecting disc-like portions increasing in size toward the dome-shaped tip; and a first projecting disc-like portion positioned closest to said moisture absorbent end piece and having a diameter larger than said dome shaped end piece; and separation areas located between said projecting disc-like portions. The swab of the patent features no douching action, and can only be adapted for vaginal scrubbing as usual.

It is known from the above descriptions of the prior art that there is no disclosure of a vaginal cleansing device featuring both douching and scrubbing effects. Further, a vaginal cleansing device featuring a counterflow preventer arranged inside the conduit thereof has not been disclosed by the prior art.

Whereas the foregoing problems have not been overcome by the prior art, the inventor of the present invention believes that people shall change the viewpoints to allay the worries that vaginal douching will degrade self defensive system of the vagina, and vaginal douching should be performed by medical professionals, and the use of unboiled water for vaginal douching will lead to vaginal infections.

SUMMARY OF THE INVENTION

To this end, an object of the present invention is to provide a self service cleaning device for woman, comprising:
- a handle having a connector at its one end, the handle being removably connected with a water supply pipe by the connector; and
- a flexible conduit having one end connected with the handle and the other end which has a curved portion with a closed top end corresponding to a curvature of vagina, wherein an opening is arranged at an introverted segment of the curved portion, and a plurality of outlets are orderly arranged on a circumferential surface of the curved portion, a plurality of circular protrusions are projecting outwardly and radially from the circumferential surface; and a counterflow preventer is arranged around an inlet of the flexible conduit.

According to the invention, the self service cleaning device for woman is strucutally simple, easy in operation, portable and capable of both douching and scrubbing, such that it can be adapted for sufficiently cleansing the entire vagina to reduce the chance of developing vaginal diseases and infections, including AIDS diseases, by 70% or above. The circular protrusions on the flexible conduit enable a gentle rubbing of the walls of vagina, producing physical and mechanical cleaning effects. Further, the arrangement of the counterflow preventer could prevent the loss of the cleaning solutions and agents filled into the cleaning device, and facilitate the injection of the cleaning solutions and agents into the vagina via water pressure to effect sufficient disinfection and sterilization. To this end, the self service cleaning device for woman of the present invention could be adapted not only for making douches at home, but also for performing treatments while travelling.

BRIEF DESCRIPTION OF THE DRAWINGS

The present invention will be described in more details with reference to the accompanying drawings, wherein:

FIG. 4 is a top view taken along a direction B as shown in FIG. 3;

FIG. 5 is a sectional view according to the line I-I as shown in FIG. 3;

FIG. 6 is a top view of a non-return valve as referred by A in FIG. 2;

DETAILED DESCRIPTION OF THE PREFERRED EMBODIMENTS

Figure 1:
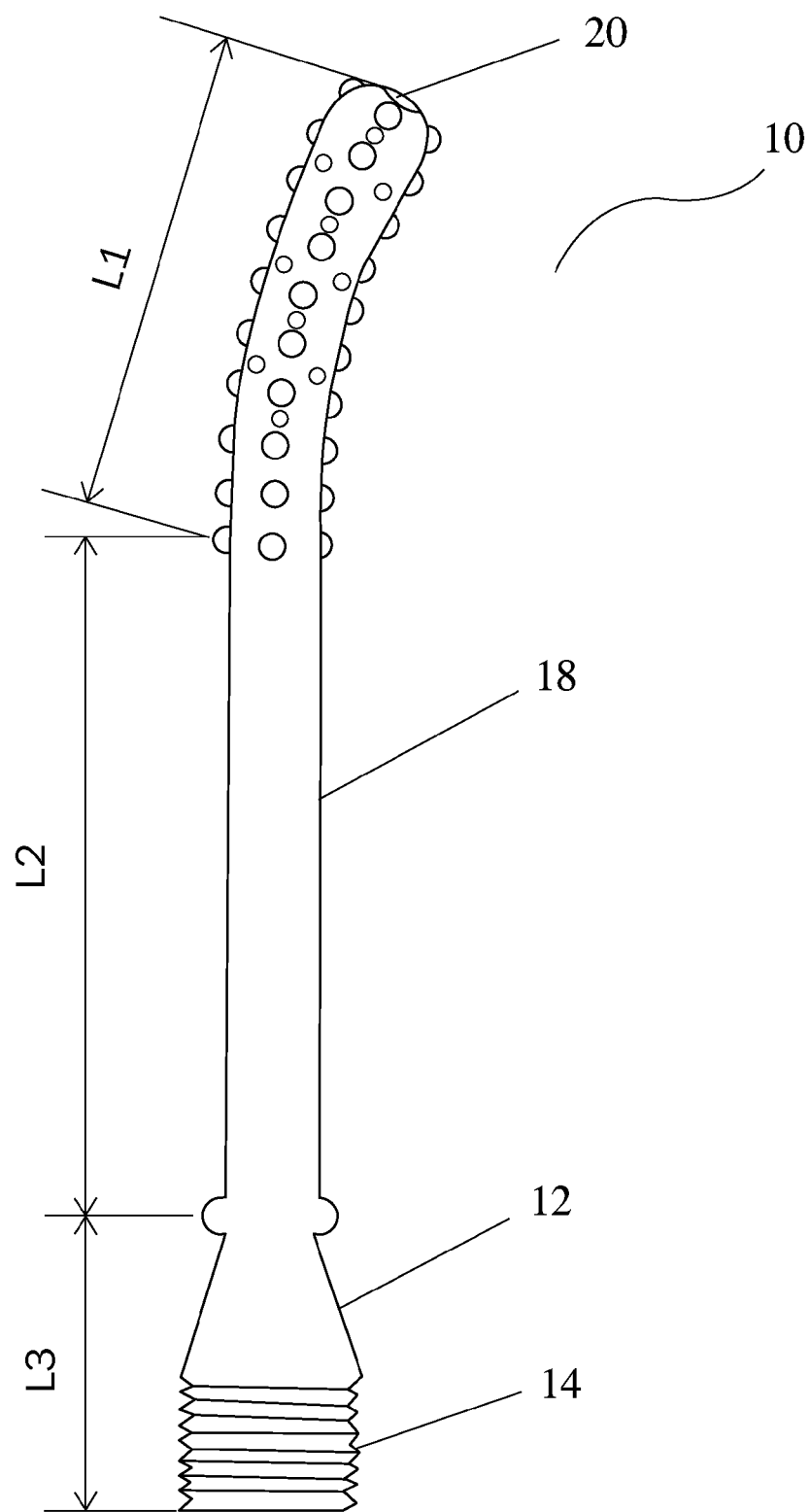
FIG. 1 is a front view of a self service cleaning device for woman of the present invention.
Figure 2:
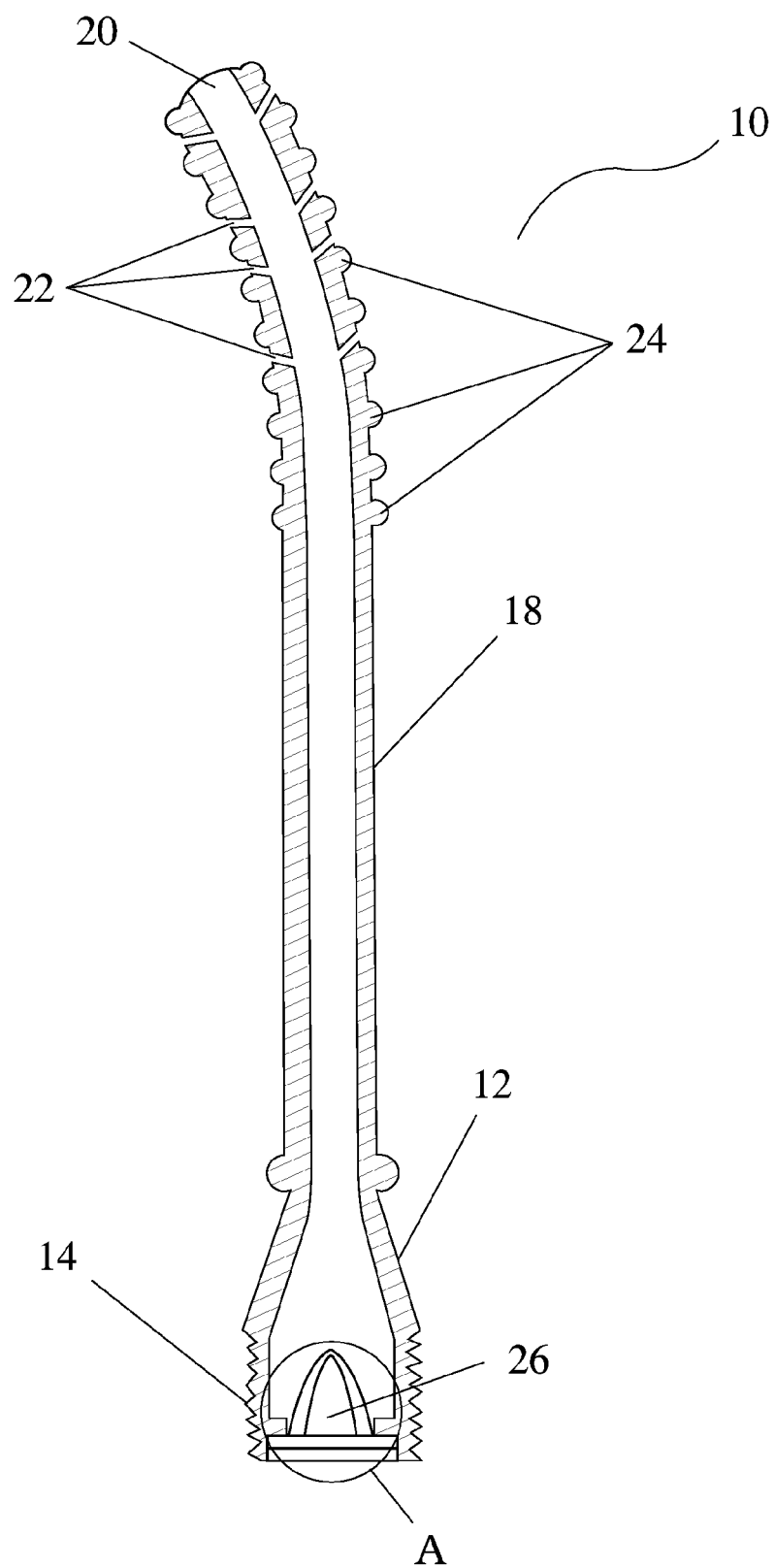
FIG. 2 is a longitudinal sectional view of FIG. 1.

Referring to FIGS. 1 and 2, a self service cleaning device for woman 10 of the present invention comprises a handle 12 and a flexible conduit 18.

Figures 7, 8:
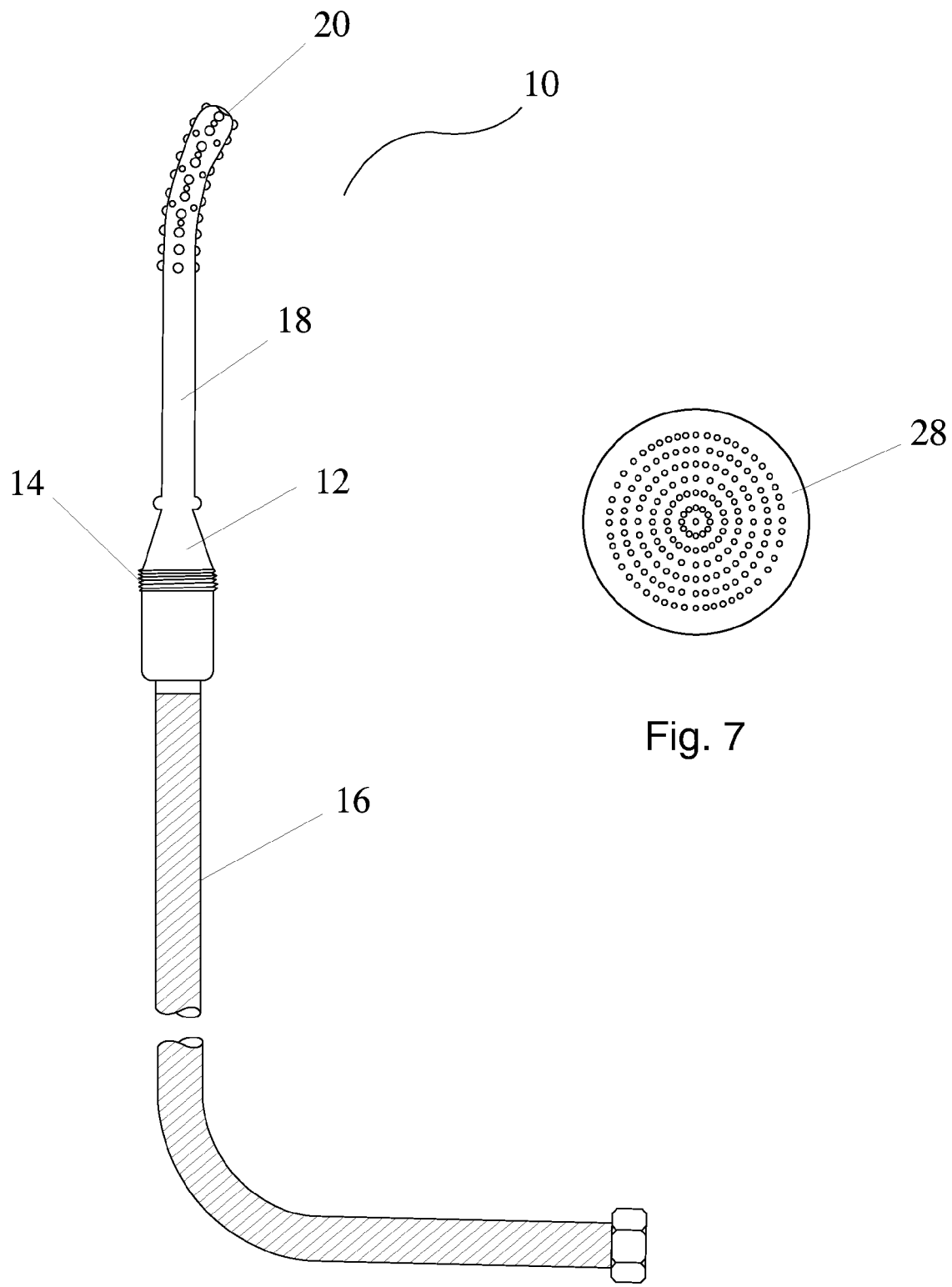
FIG. 7 is a top view of an alternative non-return sheet as referred by A in FIG. 2.
FIG. 8 is a perspective view of a self service cleaning device for woman of the present invention connected with a shower pipe used in a bathroom.

The handle 12 has a connector 14 at its one end, and the handle 12 is removably connected with a water supply pipe 16 via a threaded coupling (see FIG. 8).

The flexible conduit 18 has one end integral with the handle 12, this end could be firmly connected with the handle 12 in a threading, bonding, snap fit, press fit or taper fit manner. The flexible conduit 18 has the other end which has a curved portion L1 with a closed top end which slightly expands, corresponding to a curvature of vagina. The curved portion has a curvature radius R of 135-145 mm, and preferably of 140 mm. An opening 20 is arranged at an introverted segment of the curved portion L1, having a diameter of 4-8 mm, and preferably of 6 mm, and in particular is arranged at the second row of the outlets adjacent to the top of the introverted segment of the curved portion L1. A cleaning solution or a suitable amount of medicament can be injected from the opening 20, in order to prevent the water going into the uterus of the user. The flexible conduit has an outer diameter of 8-13 mm, preferably of 11 mm, and an inner diameter of 4-8 mm, preferably of 6 mm, while its diameter at the top end is 10-15 mm, and preferably of 13 mm.

Figure 3:
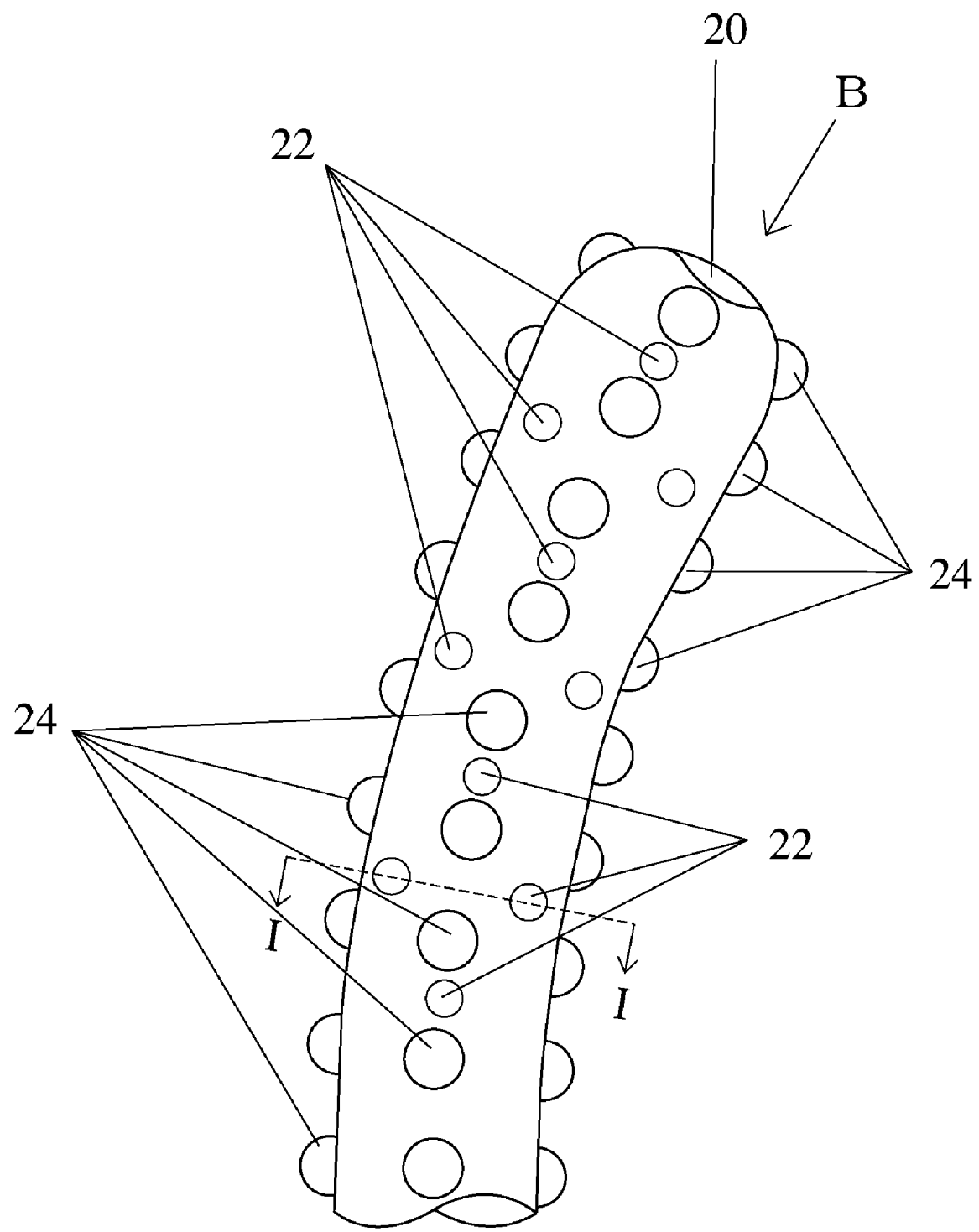
FIG. 3 is a partial enlarged view of a curved portion as shown in FIG. 1.

Referring to FIGS. 3-5, a plurality of outlets 22 are orderly arranged on a circumferential surface of the curved portion L1, and a plurality of circular protrusions 24 are outwardly and radially projecting from the circumferential surface. In particular, there are twenty-eight outlets 22 arranged on the circumferential surface of the curved portion L1, and each of the outlets 22 has a diameter of 1-3 mm, and preferably of 2 mm. The twenty-eight outlets 22 are orderly distributed on seven longitudinally spaced respective circumferences, each of the spaced circumferences carries four of the outlets 22. Such a design allows the cleaning action of a fluid flow and prevents the adverse effect to the skin mucosa due to the impact force of the fluid. In this embodiment, the number of the circular protrusions 24 is fifty-five, and each of the circular protrusions has a diameter of 2-4 mm, and preferably of 3 mm. The fifty-five circular protrusions 24 are orderly distributed on eleven circumferences, which are longitudinally spaced from those circumferences on which the outlets 22 are arranged on the curved portion L1. Each of the eleven circumferences carries five of the protrusions 24 and is longitudinally spaced from circumferences on which the outlets are arranged. There exist merely the circular protrusions 24 on the ninth and eleventh circumferences which have no outlets arranged thereon.

Referring again to FIG. 1, both the handle 12 and the flexible conduit 18 of the cleaning device 10 are made of silicon rubber. The cleaning device 10 has a length of 170-180 mm, and preferably of 175 mm, wherein the curved portion has a length of 55-65 mm, and preferably of 60 mm, the connector has a length of 30-40 mm, and preferably of 35 mm, while the rest of the cleaning device has a length of 75-85 mms, and preferably of 80 mm.

Referring to FIG. 2, a counterflow preventer is disposed in the vicinity of an inlet of the flexible conduit 18. The counterflow preventer as shown in FIGS. 2 and 6 is a non-return valve 26 which consists of four clacks and is made of silicon rubber. Each clack has a thickness of 0.1-0.5 mm, and preferably of 0.3 mm. The counterflow preventer as shown in FIG. 7 is a non-return sheet 28, which is made of silicon rubber and has an outer diameter of 12-16 mm, and preferably of 14 mm, and a thickness of 1-3 mm, and preferably of 2 mm. A plurality of bores having a diameter of 0.2 mm are concentrically distributed on the non-return sheet 28. As the silicon rubber is soft, resilient and features with a resistance to deformation, thereby it eliminates discomfort to women due to the employment of plastic materials adopted in prior art cleaning devices for woman.

In use, after the shower head in the bathroom is screwed out, the self service cleaning device for woman 10 of the present invention is connected to the water supply pipe 16 of the shower by the connector 12 via a threaded coupling, as shown in FIG. 8.

After switching on the heater and adjusting the temperature of the water to approximately 39-42° C., a user may then injects a suitable amount of cleaning solution—such as 10 ml—from the opening 20 arranged at the introverted segment of the curved portion L1. As the counterflow preventer is disposed in the vicinity of the inlet of the flexible conduit 18, the cleaning solution could be retained in the flexible conduit. The user may take a standing position for cleansing and insert the cleaning device 10 containing the cleaning solution as a lubricant into the vagina. The cleaning device may be slowly inserted with respect to the respective figure and sensation of the user, until the device reaches the posterior wall of the vagina.

Now, the user can switch on the water valve and inject the cleaning solution into the vagina with a water flow at a pressure of one second. The process allows the dilution of the cleaning solution 10 times such that the user can use a concentrated cleaning solution which does not irritate the skin and mucous membrane. Afterwards, the user can switch off the water valve, and hold and move the handle 12 back and forth for establishing a thorough contact between the cleaning solution and the vaginal rugae as well as the fornix around the cervix, and then the water valve is switched on again for vaginal douching, which may last for 1 to 2 minutes.

Should a further treatment is needed after cleansing, a suitable amount of medicament may be injected via the opening 20, and then the user can turn the water valve on for one second so that the medicament therein is carried in the vagina by the action of the water flow and provides a treatment effect without douching t.

By making use of the cleaning device of the present invention for vaginal douching in compliance with the foregoing steps, the positive rate of vaginal diseases is reduced from a pre-douching level of (+++) to a post-douching level of (+) according to the result of a smear examination of vaginal secretion.

According to the clinical observations, the employment of the self service cleaning device of the present invention, and particularly, the use of the present cleaning device for vaginal douching after an unsafe sexual intercourse, the chance of getting infected with vaginal diseases or virus, including AIDS virus, could be reduced by up to 70% or above. In addition, when an infection occurs, the user can use the present device for preliminary douching and then fill it with liquid medicine or pharmaceutical composition for further cleansing, the therapeutic effectiveness would be even more prominent.

While the present invention has been described in details with references to above preferred embodiments, it will be understood by those skilled in the art that various alterations and modifications may be made thereto without departing from the design philosophy and spirit of the invention, and all such alteration or modification shall fall into the scope of the present invention.

What is claimed is:

1. A self service cleaning device for women, comprising:
   a handle having a connector at its one end, the handle being removably connected with a water supply pipe by the connector; and
   a flexible conduit having one end connected with the handle and the other end which has a curved portion with a closed top end corresponding to a curvature of vagina, wherein an opening is arranged at an introverted segment of the curved portion, and a plurality of outlets are orderly arranged on a circumferential surface of the curved portion, a plurality of circular protrusions are projecting outwardly and radially from the circumferential surface; and
   a counterflow preventer is arranged around an inlet of the flexible conduit;
   wherein the opening is arranged at the second row of the outlets adjacent to the top of the introverted segment of the curved portion and has a diameter of 4-8 mm; and
   the plurality of outlets each has a diameter of 1-3 mm, and the circular protrusions each has a diameter of 2-4 mm.

2. The self service cleaning device for women according to claim 1, wherein the handle is integral with the flexible conduit.

3. The self service cleaning device for women according to claim 1, wherein the handle is firmly connected with the flexible conduit.

4. The self service cleaning device for women according to claim 3, wherein the handle is firmly connected with the flexible conduit in a manner of threading, bonding, snap fit, press fit or taper fit.

5. The self service cleaning device for women according to claim 1, wherein both the handle and the flexible conduit are made of silicon rubber.

6. The self service cleaning device for women according to claim 1, wherein the cleaning device has a length of 170-180 mm, wherein the connector has a length of 30-40 mm, the curved portion has a length of 55-65 mm and a radius of 135-145 mm, and the rest of the cleaning device has a length of 75-85 mm.

7. The self service cleaning device for women according to claim 1, wherein the connector and the water supply pipe is connected via a threaded coupling.

8. The self service cleaning device for women according to claim 1, wherein the opening has a diameter of 6 mm.

9. The self service cleaning device for women according to claim 1, wherein:
   the plurality of outlets are twenty-eight outlets; and
   the twenty-eight outlets are orderly distributed on seven longitudinally spaced circumferences, each of the circumferences carries four of the outlets.

10. The self service cleaning device for women according to claim 1, wherein the circumferential surface of the curved portion has fifty-five circular protrusions; wherein the fifty-five circular protrusions are orderly distributed on eleven longitudinally spaced circumferences, each of the circumferences carries five of the circular protrusions and is longitudinally spaced from the circumferences on which the outlets are distributed.

11. The self service cleaning device for women according to claim 1, wherein the flexible conduit has an outer diameter of 8-13 mm and an inner diameter of 4-8 mm, wherein the curved portion of the flexible conduit slightly expands in the vicinity of the top end with a diameter of 10-15 mm.

12. The self service cleaning device for women according to claim 1, wherein the counterflow preventer is a non-return valve consisting of four clacks.

13. The self service cleaning device for women according to claim 11, wherein the clack is made of silicon rubber and has a thickness of 0.1-0.5 mm.

14. The self service cleaning device for women according to claim 1, wherein the counterflow preventer is a non-return sheet.

15. The self service cleaning device for women according to claim 14, wherein the non-return sheet is made of silicon rubber on which a plurality of bores having a diameter of 0.2 mm are concentrically distributed.

16. The self service cleaning device for women according to claim 15, wherein the non-return sheet has an outer diameter of 12-16 mm and a thickness of 1-3 mm.

17. The self service cleaning device for women according to claim 16, wherein the outer diameter of non-return sheet is 14 mm and the thickness of the non-return sheet is 2 mm.

* * * * *